(12) United States Patent
Lindgren et al.

(10) Patent No.: US 8,374,705 B2
(45) Date of Patent: Feb. 12, 2013

(54) IMPLANTABLE MEDICAL LEAD WITH HOUSING INTEGRITY INDICATOR

(75) Inventors: Anders Lindgren, Täby (SE); Charlotta Bergman, Stockholm (SE); Per Axelson, Stockholm (SE); Jan Ljungström, Hässelby (SE)

(73) Assignee: St. Jude Medical AB, Jarfalla (SE)

( * ) Notice: Subject to any disclaimer, the term of this patent is extended or adjusted under 35 U.S.C. 154(b) by 212 days.

(21) Appl. No.: 12/917,637

(22) Filed: Nov. 2, 2010

(65) Prior Publication Data

US 2011/0264177 A1    Oct. 27, 2011

(30) Foreign Application Priority Data

Apr. 23, 2010   (EP) .................................. 10160892

(51) Int. Cl.
*A61N 1/05* (2006.01)
(52) U.S. Cl. ......... 607/116; 607/122; 607/126; 607/127
(58) Field of Classification Search .................... 607/116
See application file for complete search history.

(56) References Cited

U.S. PATENT DOCUMENTS

| | | | | |
|---|---|---|---|---|
| 3,954,102 | A | * | 5/1976 | Buuck .............................. 600/40 |
| 3,971,754 | A | * | 7/1976 | Jurecic .......................... 523/117 |
| 4,185,626 | A | * | 1/1980 | Jones et al. ..................... 602/41 |
| 5,571,156 | A | | 11/1996 | Schmukler |
| 5,733,787 | A | * | 3/1998 | Messenger et al. ............. 436/98 |
| 6,813,521 | B2 | * | 11/2004 | Bischoff et al. ............... 607/122 |
| 7,454,249 | B1 | | 11/2008 | Bornzin et al. |
| 7,532,939 | B2 | | 5/2009 | Sommer et al. |
| 2008/0167701 | A1 | | 7/2008 | John et al. |

\* cited by examiner

*Primary Examiner* — Christopher D Koharski
*Assistant Examiner* — Michael Carey

(57) ABSTRACT

An implantable medical lead has at least one electric conductor running along a lead body and electrically interconnecting at least one electrode at the distal portion of the lead with at least one lead terminal at the proximal portion of the lead. The lead also has at least one closed channel running along at least a portion of the lead body. The closed channel contains an extracorporeally detectable detection substance. A rupture to the lead will cause the detection substance to leak out of the channel and outside of the lead body. Lead damage can be confirmed by the absence of or a reduced amount of said detection substance inside the lead.

13 Claims, 7 Drawing Sheets

IMPLANTABLE MEDICAL LEAD WITH HOUSING INTEGRITY INDICATOR

BACKGROUND OF THE INVENTION

1. Field of the Invention

The present invention generally relates to implantable medical leads, and in particular to an implantable medical lead that allows detection of lead insulation damages following implantation and to a method of detecting such a lead insulation damage.

2. Description of the Prior Art

Today implantable medical devices (IMDs), such as pacemakers, cardioverters and defibrillators, among others, are typically connected to heart or nervous tissue by means of one or more implantable medical leads. These implantable medical leads provide electrical contact between the tissue and the IMD, which is generally implanted some distance from the target tissue to be sensed, paced or otherwise treated by the IMD.

The implantable medical lead is a vulnerable component of the IMD system and it can easily get damaged by inappropriate handling during implantation with serious consequences as a result. It is also a well known fact that the hostile environment of an implanted medical lead in addition to the implantation technique used at implantation may cause adverse events debuting later on in time. Illustrative examples include subclavian crush phenomena, conductor breakages, lead insulation damages and various types of lead abrasions.

Symptoms of lead damages may vary from cosmetic to hazardous ones. What they all have in common is that their symptoms mostly debut intermittently, progress gradually and are often very difficult to diagnose due to lack of appropriate tools.

Today the analysis of potential lead damages are performed by analysis of X-rays, intracardiac EGM (IEGM) and lead impedance measurements in combination with lead provocative movements. However, it is very hard to detect small lead damages, such as minor ruptures to the insulation material of the implantable medical lead using prior art techniques. Furthermore, IEGM and lead impedance measurements are not specific tools in order to consistently diagnose lead damages since they are generally not sensitive enough. It is therefore very hard to discriminate between lead insulation damages and other symptoms from IEGM and lead impedance measurements.

Lead damages might cause inappropriate therapy, such as high voltage defibrillation, or inhibition of therapy, such as inhibition of pacemaker pulses. It is therefore important to find an easy, cheap and reliable way to detect and verify lead damages before they create discomfort or injuries to the patient.

U.S. Pat. No. 7,532,939 discloses an active fixation medical lead having a tracking member extending from the distal end of the lead body, through the helical fixation member and outward from the distal end. The tracking member is used to facilitate tracking of the medical lead during implantation. After implantation a radio-opaque solution can be injected through the lumen of the medical lead to thereby leak out of the distal end. There the radio-opaque solution causes residual staining of the surrounding tissue and thereby facilitates fluoroscopic imaging at the implant site.

SUMMARY OF THE INVENTION

A general object of the invention is to provide a technique that facilitates verification of lead damages and in particular lead insulation ruptures of implantable medical leads.

It is a particular object to provide an implantable medical lead designed to allow easy verification of lead insulation ruptures.

These and other objectives are met by embodiments as disclosed herein.

Briefly, an implantable medical lead has a lead body through which at least one conductor runs. The at least one conductor is electrically connected to an electrode provided in connection with a distal portion of the implantable medical lead. The opposite end of the at least one conductor is electrically connected to a lead terminal arranged in connection with the proximal portion of the implantable medical lead that is designed to be connectable to an implantable medical device.

The implantable medical lead has at least one closed channel running along at least a portion of the lead body. The closed channel comprises a detection substance. If a rupture occurs in the implantable medical lead and in particular in an insulating tubing of the lead the detection substance will leak out of the closed channel and outside of the implantable medical lead. A lead rupture is thereby confirmed by the absence of or a reduced amount of the detection substance in the closed channel, which may be verified by the presence of the detection substance outside of the closed channel and outside of the implantable medical lead.

An embodiment relates to a method of detecting a lead insulation rupture based on a reduced amount of the detection substance in the implantable medical lead.

The embodiments allow easy but reliable identification of lead simulation ruptures including very small ruptures at an early stage.

DESCRIPTION OF THE PREFERRED EMBODIMENTS

Throughout the drawings, the same reference numbers are used for similar or corresponding elements.

The embodiments generally relate to an implantable medical lead designed to facility detection of lead damages and ruptures, in particular lead insulation ruptures, following implantation of the lead in an animal, preferably a mammalian and more preferably a human patient.

According to the embodiments the implantable medical lead has at least one closed channel that is at least partly filled with a detection substance. This level or amount of the detection substance in the closed channel is utilized as a confirmation of the presence of a damage or rupture to the implantable medical lead and in particular lead insulation ruptures or damages. The reduced amount of the detection substance can be verified as the absence of or a reduced amount of the detection substance inside the closed channel, such as by imaging techniques. Alternatively, the reduced amount of the detection substance in the closed channel can be verified by the presence of the detection substance outside of the closed channel and the implantable medical lead.

Figure 1:
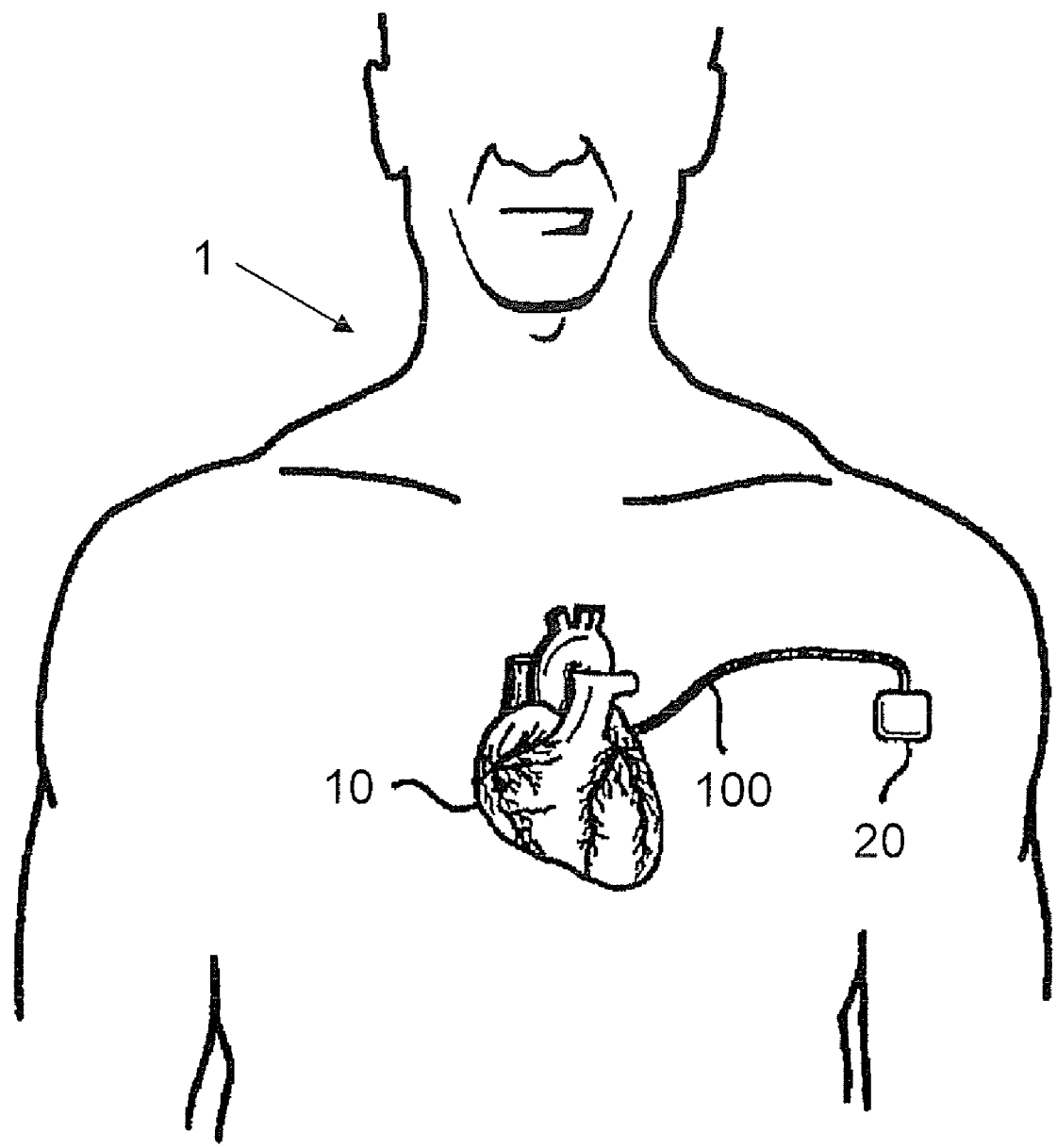
FIG. 1 is a drawing illustrating a human patient with an implantable medical device connected to an implantable medical lead according to an embodiment.

FIG. 1 schematically illustrates a human patient 1 having an implantable medical lead 100 according to an embodiment. The implantable medical lead 100 is preferably designed to be mechanically and electrically connectable to an implantable medical device (IMD) 20. The implantable medical lead 100 thereby forms a bridging unit that allows the IMD 20 to sense and/or provide therapy to a target tissue, represented by a heart 10 in the figure, through the implantable medical lead 100.

The implantable medical lead 100 is advantageously designed to be connectable to an IMD 20 in the form of a pacemaker, cardioverter or defibrillator capable of sensing and providing therapy to a patient's 1 heart 10. The embodiments are, however, not limited to cardiac-associated IMDs but also apply to implantable medical leads 100 designed to be connectable to other types of IMDs 20 including, but not limited to, drug pumps, neurological stimulators, physical signal recorders, oxygen sensors, or the like.

Figure 2:
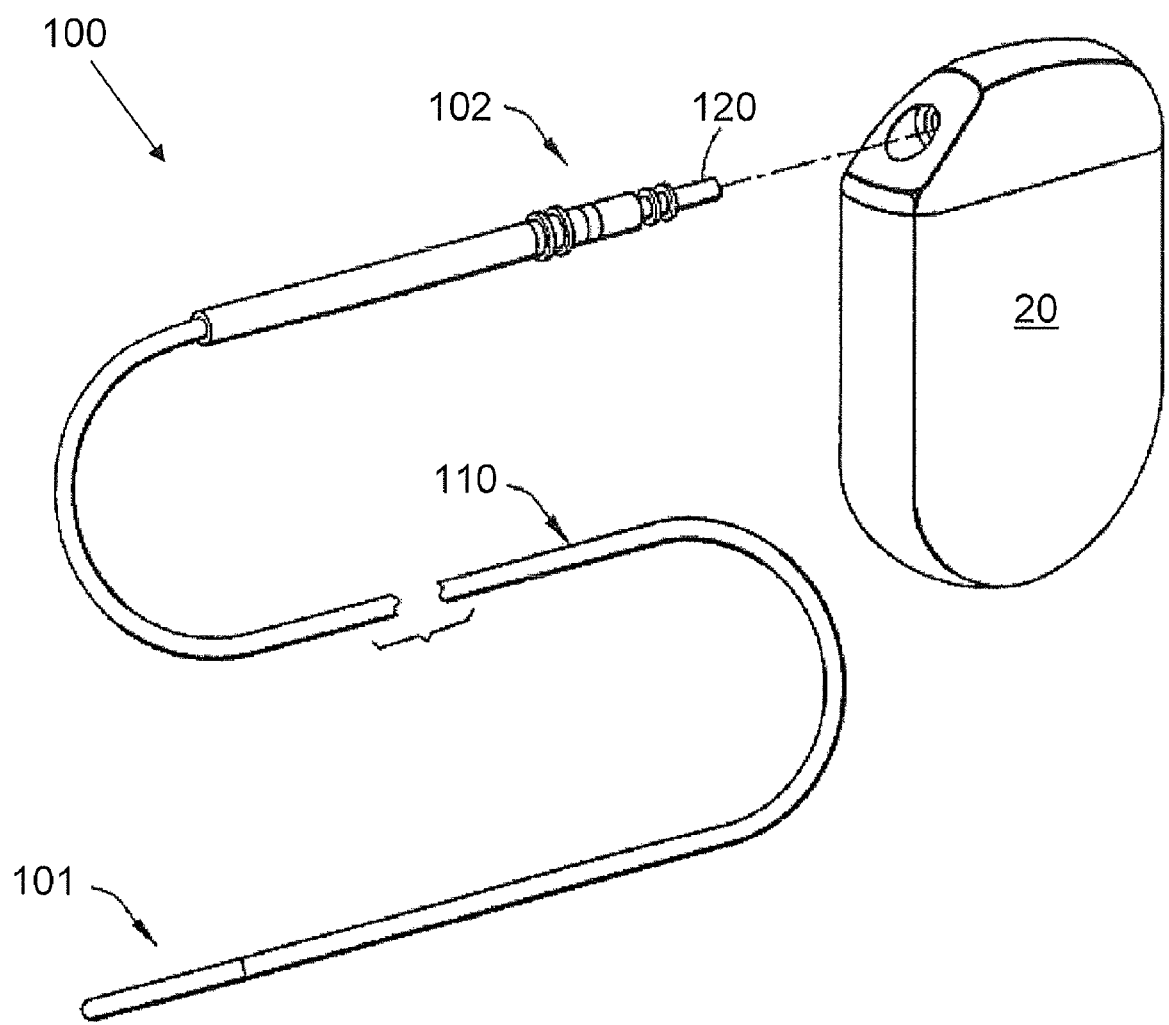
FIG. 2 schematically illustrates an implantable medical lead according to an embodiment connectable to an implantable medical device.

FIG. 2 schematically illustrates an implantable medical lead 100 and how it can be connected to an IMD 20. The implantable medical lead 100 comprises a first or proximal end or portion 102 constructed to be mechanically and electrically connected to the IMD 20. This proximal portion 102 preferably comprises at least one lead or electrode terminal 120 that will be electrically connected to at least one matching terminal in the IMD 20 when the implantable medical lead 100 is attached to the IMD 20. The second or distal end or portion 101 of the implantable medical lead 100 is designed to be attached to or in connection with the tissue that the IMD 20 should sense and/or provide therapy to. The proximal portion 102 and the distal portion 101 are interconnected by a lead body 110 as illustrated in the figure.

The lead body 110 has at least one electric conductor running along the body 110 and is electrically connected to a lead terminal 120 in the proximal portion 102 and an electrode in connection with the distal portion 101. The implantable medical lead 100 can comprise multiple electrodes in the distal portion 101. In such a case, each electrode comprises at least one respective conductor running along the lead body 110 and being electrically insulated from the at least one conductor of the other electrode(s). The at least one conductor of each electrode terminates at the proximal portion 102 in a lead terminal 120 that is electrically connectable to the IMD 20.

According to the embodiments, this lead body 110 comprises and encloses at least one closed channel comprising a detection substance, which is further described herein.

Figure 3:
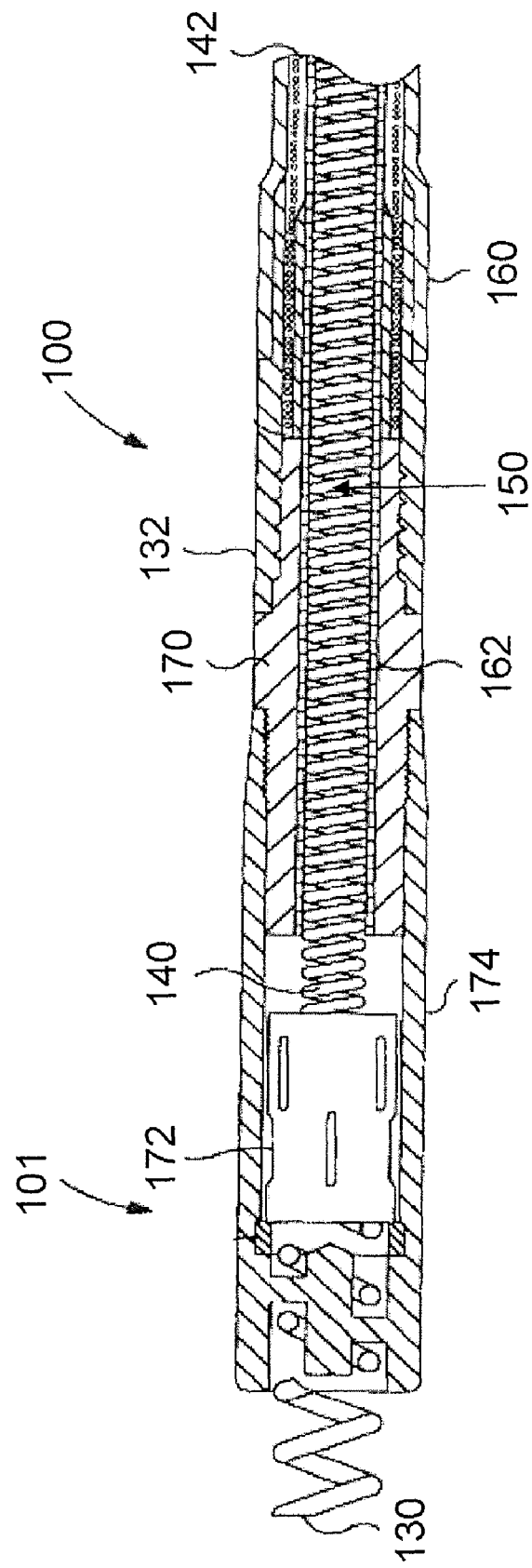
FIG. 3 is a cross-sectional view of a distal portion of an implantable medical lead according to an embodiment.

FIG. 3 illustrates a greatly enlarged cross-sectional view of an embodiment of the distal portion 101 of an implantable medical lead 100 of the active fixation type. As seen, the implantable medical lead 100 has an outer flexible insulative sheath or tubing 160 made of, for instance silicone rubber, polyurethane, a mixture thereof, or the like. The outer insulative sheath 160 covers a first coiled conductor 142. The conductor 142 extends along through the lead body and terminates at its distal portion 101 where it is electrically coupled, for example by spot or laser welding, to a ring electrode 132.

Partially engaged between the ring electrode 132 and a fixation helix 130 is a ring/spacer assembly 170 that is coupled, in this embodiment, to a tip/ring spacer 174, which is typically made of silicone rubber. In addition to establishing a predetermined distance between the ring electrode 132 and the fixation helix 130, the tip/ring spacer 174 functions to define a substantially cylindrical chamber in which the remaining components are disposed as well as to define the outer surface of the electrode and fixation assembly. In the disclosed embodiment, the tip/ring spacer 174 has dimensions such that a constant lead body diameter is maintained between the fixation helix 130 and the ring electrode 132.

Extending along the length of the lead body through the ring electrode 132, the ring/spacer assembly 170 and the tip/ring spacer 174 is a second coiled conductor 140, which is insulated from the outer coiled conductor 142 by an inner insulative sheath or tubing 162 which, like the outer sheath 160 can be made of silicone rubber, polyurethane, a mixture thereof, or the like. The inner conductor 140 terminates at a substantially cylindrical crimp bus 172. The crimp bus 172, in turn is coupled to the fixation helix 130. The fixation helix 130 has the dual function of fixing the implantable medical lead 100 to the myocardium or other target tissue and functions as a sensing/pacing electrode.

In an alternative embodiment of an active fixation lead, the ring electrode is omitted. In other words, the lead is of the unipolar type. The electrode is then the active helix fixation electrode or another type of active fixation electrode.

The implantable medical lead 100 also comprises a closed channel 150 running along at least a portion of the lead body. In the illustrated embodiment this closed channel 150 constitutes the closed inner lumen defined by the inner coiled electric conductor 140. Thus, the inner coiled conductor 140 has an inner lumen that is closed in the distal end by the crimp bus 172. During implantation the proximal end of the inner lumen 150 may be open to allow introduction of a guide wire through the inner lumen 150. In such a case, the detection substance can still be present inside the lumen or is added thereto once the guide wire has been removed. In the former case, the amount of the detection substance inside the lumen 150 is not too high to thereby prevent the detection substance from spilling over when the guide wire is introduced inside the lumen 150. Once the implantable medical lead 100 has been guided through the human body to correct implantation site, the guide wire is removed. Additional detection substance can then be filled into the lumen 150 if desired. If the lumen 150 did not contain any detection substance prior introduction of the guide wire, the detection substance is poured into or added to the lumen 150 once the guide wire has been removed. The proximal end of the lumen 150 is then closed, for instance with a channel plug or some other fluid tight unit. Alternatively, the introduction of the proximal portion of the implantable medical lead 100 into an IMD can cause the closure of the open lumen end to thereby form a closed channel 150.

In an alternative embodiment, the closed channel is formed outside of the inner coiled conductor 140 but within the lumen of the outer coiled conductor 142. There is then a small distance between the inner insulative sheath 162 and the outer coiled conductor 142 in which the detection substance is filled. However, this alternative embodiment requires a somewhat larger lead diameter due to the introduction of the extra space between the inner insulative sheath 162 and the outer coiled conductor 142. The embodiment is therefore mainly for those application where the lead diameter is not a critical issue.

Figure 4:
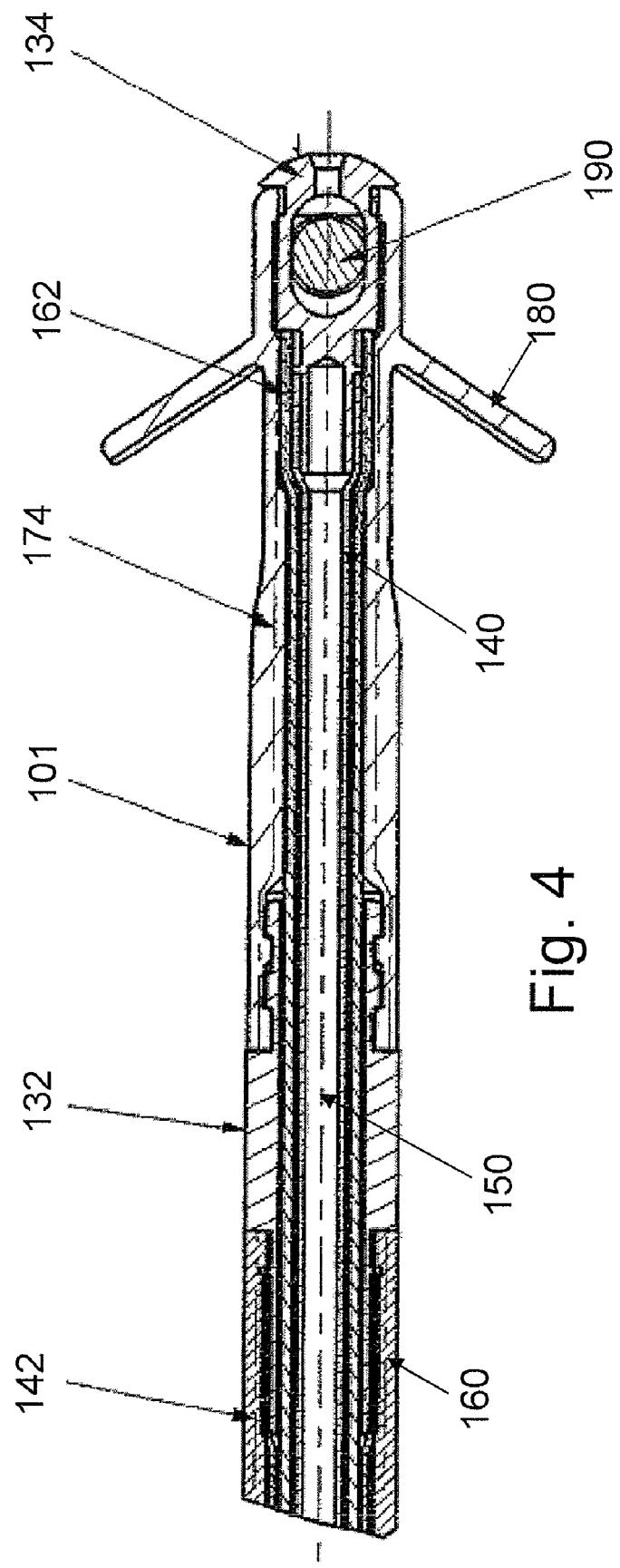
FIG. 4 is a cross-sectional view of a distal portion of an implantable medical lead according to another embodiment.

The implantable medical lead must not necessarily be of a so-called active fixation type. FIG. 4 illustrates an enlarged cross-sectional view of an implantable medical lead of passive fixation type. The lead body has an outer flexible insulative sheath or tubing 160 covering a first coiled conductor 142 extending along the lead body and terminating at a ring electrode 132 or electrically coupled to the ring electrode through a crimp sleeve (not illustrated).

A second inner coiled conductor 140 is electrically insulated from the first conductor 142 by an inner insulative sheath or tubing 162. The inner conductor 140 is electrically connected to a tip electrode 134. The lead tip may also optionally be equipped with a steroid plug 190, the use of which is well known in the art. Passive fixation of the implantable medical lead at a correct position in a patient body is achievable by a tine assembly 180.

It is anticipated that the implantable medical lead partly illustrated in FIG. 4 may alternatively be of a unipolar type. In such a case, the ring electrode 132 and its associated coiled conductor 142 can be omitted.

In similarity to the implantable medical lead of FIG. 3, the inner lumen 150 of the inner coiled conductor 140 defines and constitutes a closed channel 150 comprising the detection substance. The discussion above in connection with FIG. 3 with regard to filling the lumen with the detection substance prior and/or after removal of an optional guide wire and the usage of a closed channel between the inner insulative sheath 162 and the outer conductor coil 142 can also be applied to the implantable medical lead of passive fixation type.

The implantable electrode of the invention can also be used in other passive fixation leads than the one illustrated in FIG. 4, i.e. having another set of distal lead components.

Figure 5:
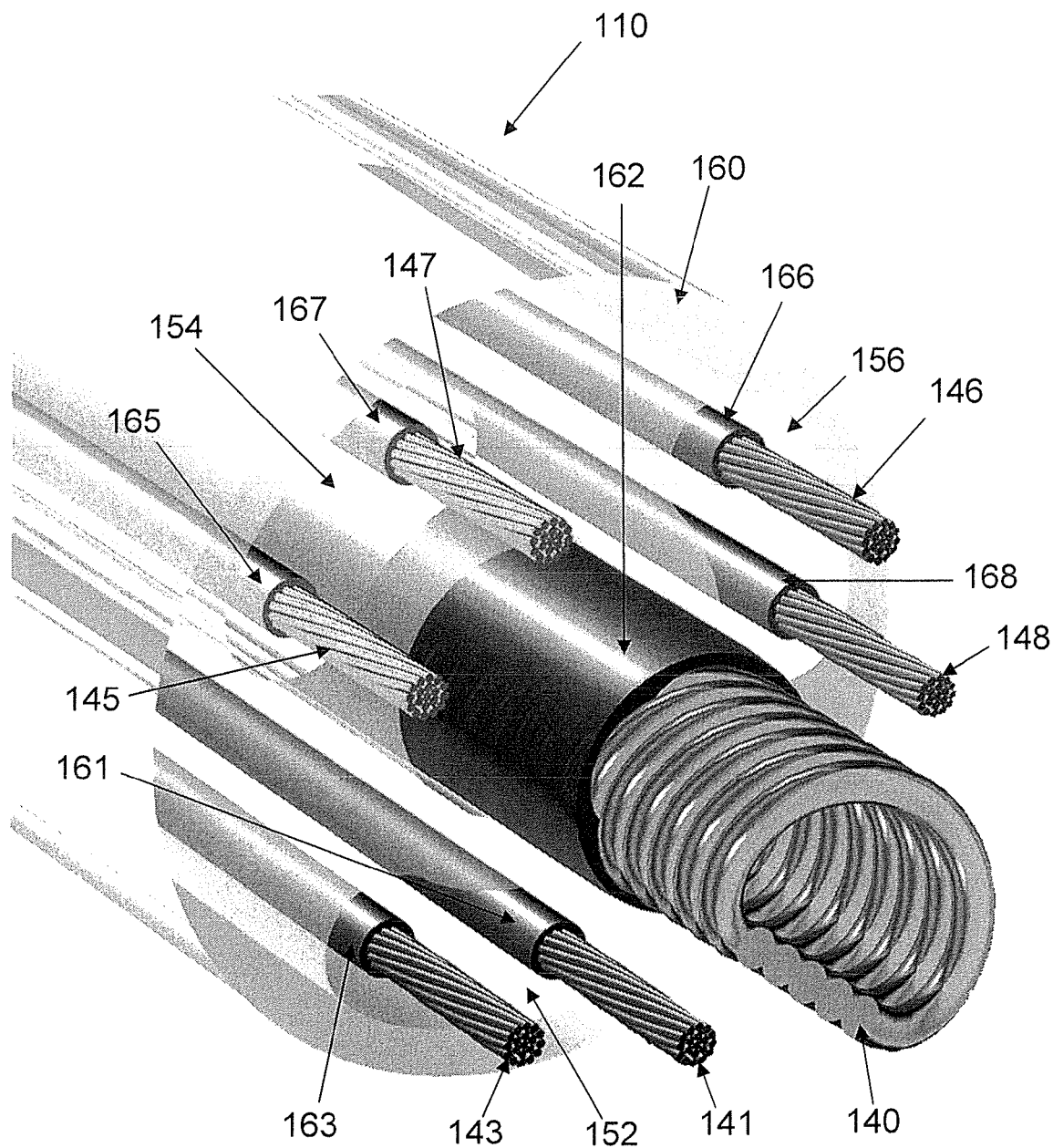
FIG. 5 is a partly cross-sectional view of an implantable medical lead according to a further embodiment.

FIG. 5 is a partly cross-sectional view of an implantable medical lead according to a further embodiment. This implantable medical lead is of a so-called multipolar type implying that it comprises more than two electrodes in the distal end. As is seen in the figure, this particular type of implantable medical lead comprises seven conductors 140, 141, 143, 145, 146, 147, 148. One of the conductors is a coiled electric conductor 140 centrally positioned inside the lead body 110. The other conductors 141, 143, 145, 146, 147, 148 are peripherally positioned inside the lead body 110 in an insulative sheath or tubing 160 relative the central conductor 140. Each conductor 140, 141, 143, 145, 146, 147, 148 preferably comprises a respective insulative sheath or tubing 161, 162, 163, 165, 166, 167, 168 around the conductor 140, 141, 143, 145, 146, 147, 148 to electrically insulate the conductor 140, 141, 143, 145, 146, 147, 148 from the other conductors 140, 141, 143, 145, 146, 147, 148.

In an embodiment, the implantable medical lead can be a heptapolar lead preferably having one fixation helix acting as electrode and being electrically connected to the coiled electric conductor 140. Alternatively, the implantable medical lead is of the passive fixation type and the central electric conductor 140 is instead connected to a tip or ring electrode. Each of the peripheral conductors 141, 143, 145, 146, 147, 148 is then electrically connected to a respective ring electrode that is provided in the distal portion of the implantable medical lead. Compared to the embodiments of FIGS. 3 and 4, such an implantable medical lead would then have six or seven spaced apart and electrically separated ring electrodes provided at different locations along the distal portion.

In an alternative and preferred embodiment, the implantable medical lead is of a quadropolar type. In such a case, the implantable medical lead preferably has a fixation helix that operates as an electrode and is electrically connected to the coiled conductor 140 or is of the passive fixation type as described above. The distal portion of the implantable medical lead further has three spaced apart and electrically separated ring electrodes or coils arranged at different locations along the distal portion. Each such ring electrode is then electrically connected to a pair of peripheral conductors. For instance, conductors 141, 143 are electrically connected to a first ring electrode, conductors 145, 147 are electrically connected to a second ring electrode and a third ring electrode is electrically connected to conductors 146, 148.

The outer insulative sheath 160 around the coiled conductor 140 and including the peripheral conductors 141, 143, 145, 146, 147, 148 has at least one closed channel 152, 154, 156 that is peripherally provided in the outer insulative sheath 160 relative the centrally positioned electric conductor 140. FIG. 5 illustrates three such closed channels 152, 154, 156. Each pair of peripheral conductors 141, 143, 145, 146, 147, 148 then runs along a respective closed channel 152, 154, 156 as shown in FIG. 5. This is, however, merely an illustrative embodiment. In alternative embodiments, the at least one closed channel 152, 154, 156 can be provided elsewhere in the peripheral part of the outer insulative sheath 160, i.e. outside of the central electric conductor 140. For instance, a closed channel 152, 154, 156 can be provided in the part of the outer insulative sheath 160 that is present between two neighboring pairs of peripheral conductors 141, 143, 145, 146, 147, 148.

The implantable medical lead can have a single closed channel or multiple, i.e. at least two, parallel or at least partly parallel closed channel 152, 154, 156. Three closed channels 152, 154, 156 as illustrated in FIG. 5 is therefore merely an illustrative example.

The at least one closed channel of the implantable medical lead can run along the entire length of the lead body or at least substantially the whole length. In such a case, the at least one closed channel starts from the distal end or close thereto and runs all the way to the proximal end or close thereto. This is preferred since then a rupture or damage in the lead insulation anywhere along the lead body will cause the detection substance to leak out of the closed channel and outside of the implantable medical lead, which can be detected as the absence or reduced amount of the detection substance in the closed channel or the presence of the detection substance outside of the implantable medical lead. If the closed channel instead would run along merely a portion of the lead body, lead insulation ruptures can occur in other parts of the implantable medical lead where there is no closed channel. Hence, these insulation ruptures will then probably not give rise to any detection substance leakage.

If the implantable medical lead has multiple closed channels as illustrated in FIG. 5 they can be partly parallel or end substantially at the same location along the lead body as another closed channel starts. It then means that even though none of the closed channel extends by itself along the whole length of the lead body they will together cover at least a major part of the lead length.

Figure 6:
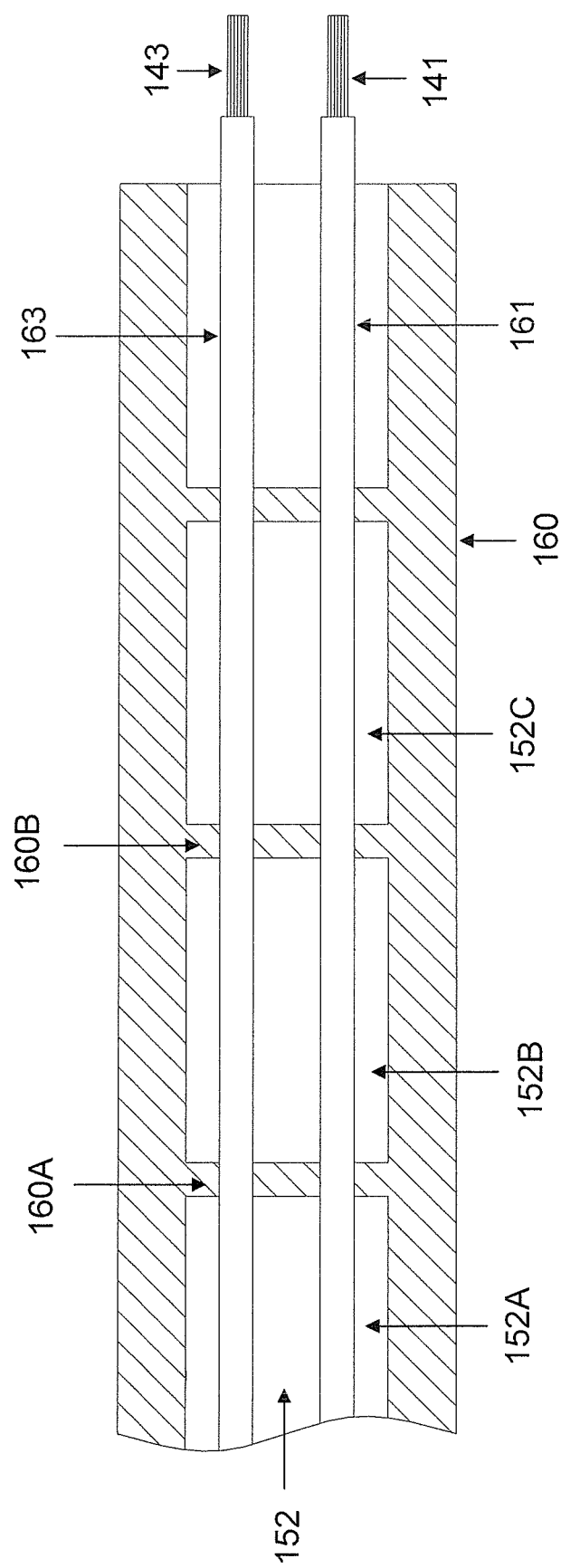
FIG. 6 schematically illustrates the concept of a multi-chamber fluid channel applied to the implantable medical lead as illustrated in FIG. 5.

It is also possible to divide a closed channel 152 into multiple sub-channels or closed compartments or chambers 152A, 152B, 152C. This concept is illustrated in FIG. 6. Each of the multiple chambers 152A, 152B, 152C is separated from the neighboring chamber(s) by respective wall(s) 160A, 160B. The chambers 152A, 152B, 152C comprises the detection substance.

If different detection substances are filled in the different chambers it can be possible to identify more accurately where along the lead body a rupture in the insulation sheath 160 has occurred by identifying the particular detection substance that leaks outside of the implantable medical lead. When substance leakage detection is performed with X-ray imaging as is further described herein, the non-leaking, intact chambers can then serve as reference and the leaking chamber can then be clearly seen from the X-ray image as the absence or reduced amount of level of detection substance in the leaking chamber.

The detection substance should be a biocompatible substance, the reduced level or amount of which in the closed channel is detectable when it has leaked through an insulation rupture or damage in the implantable medical lead. Biocompatible implies that the detection substance should not be toxic or at least not cause any significant toxicity based injuries to the human body at the substance amount that can leak out from the closed channel following a lead insulation damage. The detection substance should also not elicit any significant, health-threatening immunoreactions or allergies to the human body.

The lead insulation rupture is confirmed as a reduced amount of the detection substance in the at least one closed channel. Reduced amount implies that any amount of the detection substance in the leaking channel is lower than the initial or starting amount or level of the detection substance in the at least closed channel before the occurrence of the lead rupture. A reduced amount of the detection substance can, as is further described herein, be confirmed according to various embodiments. For instance, a reduced amount can be confirmed as the absence or a reduced amount of the detection substance inside a channel, for instance by taking an X-ray image of the implantable medical lead and using radio-opaque detection substances. Alternatively, the reduced amount of the detection substance in the channel is confirmed by the presence of the detection substance outside of the implantable medical lead. For instance, the presence of the detection substance in the blood or the urine of the patient is a confirmation of a lead insulation rupture that causes leakage of the detection substance from the closed channel and the lead.

According to the embodiments the at least one closed channel with the detection substance is fully closed prior to any lead damage. This means that the detection substance is confined inside the at least one closed channel and cannot escape therefrom. Once a lead damage, preferably a lead insulation damage, occurs a (small) rupture appears in the insulative sheath causing an opening into the closed channel, which thereby becomes open. Detection substance now starts to leak out from the channel and the lead damage can be detected based on the reduced amount of the detection substance remaining (if any) in the now opened channel.

In an embodiment, the detection substance is a detection fluid. The at least one closed channel is therefore a closed fluid channel housing the detection fluid. The detection fluid can be present in various forms in terms of viscosity. For instance, very runny fluids or liquids having comparatively low viscosity can be used. Low viscosity implies that the detection fluid will easily pour out from any ruptures or holes in the outer insulator or the implantable medical lead. Also higher viscosity fluids having a consistency that is closer to gels can be used as detection fluid as long as the fluid is capable of leaking out of the closed fluid channel upon a lead insulation damage.

In an alternative embodiment the detection substance is a solid substance, such as in the form of a powder or small particles. In the case of a lead insulation rupture blood present outside of the implantable medical lead will leak into the channel with the solid substance. The solid particles become dissolved or dispersed in the blood. The blood will thereby carry the solid particles outside of the channel and out of the implantable medical lead. The consequence of the lead insulation damage is that detection substance particles are carried by the blood out from the channel and the implantable medical lead thereby reducing the amount of detection substance present in the now opened channel.

A detection fluid according to the embodiments can be formed by dissolving or dispersing solid substance particles in a fluid or liquid, such as water. The resulting detection fluid can then be filled in the at least one closed channel as disclosed herein.

In an embodiment, the detection substance is a substance that is detectable in the blood or urine outside of the implantable medical lead following a lead fracture or damage. In such a case, a simple blood sample can be used to verify the presence of the detection substance outside of the closed channel and thereby confirm the lead insulation damage. Any substance that can be detectable in a blood sample can be used in this embodiment. In an alternative embodiment, the substance will cause a coloring of the urine of the human patient when the detection substance leaks out from the closed channel. It is then easy to verify and confirm a lead damage through the detection of a coloring of the urine. An example of such urine-coloring fluid that can be used is methylene blue.

A coloring fluid or substance leaks out from the closed channel in order to color the urine following a lead insulation damage. A limitation with such an embodiment is that an insulation defect might be small at the beginning. The coloring of the urine might then be too small to be observed by the patient. The whole reservoir of color detection substance inside the closed channel might, thus, be emptied without giving any visual symptoms to the urine. There is also a risk of false warnings since urine can be colored by various foods and beverages.

An embodiment of the detection substance does not have these limitations of urine-coloring detection substances. This embodiment uses a radio-opaque substance and preferably an X-ray opaque substance. The X-ray opaque substance is then easily visible by taking an X-ray image of at least a part of the implantable medical lead. If a lead defect occurs causing a (small) rupture in the insulative sheath and thereby an opening to the closed channel, the X-ray opaque substance will start to leak out of the channel and the implantable medical lead. The absence of the X-ray opaque substance in the implantable medical lead or at least the reduced amount of the X-ray substance in the now opened channel is easily seen in an X-ray image and will be a visual verification of the presence of a lead insulation damage.

A further advantage of utilizing an X-ray opaque substance as detection substance is that the implantable medical lead will be clearly visibly via X-ray imaging during implantation, which significantly simplifies the implantation process. Additionally, the lead motion during the heart cycles can be observed in real time by X-ray imaging. This monitoring of the lead motion can be used to judge whether the current lead location inside the human body and/or the lead fixation to the tissue is satisfactory. The X-ray imaging can also be used to determine whether more lead cable has to be fed into or be withdrawn from the heart.

If the at least one closed channel comprises multiple separate chambers as illustrated in FIG. 6, intact chambers filled with X-ray opaque substance will serve as reference and an empty or at least partly empty chamber is easily and visually identifiable from an X-ray image of the implantable medical lead.

The X-ray opaque substance can be selected from among any of the prior art known X-ray opaque substances and biocompatible contrast media or agents that are today used within the medical field.

Figure 7:
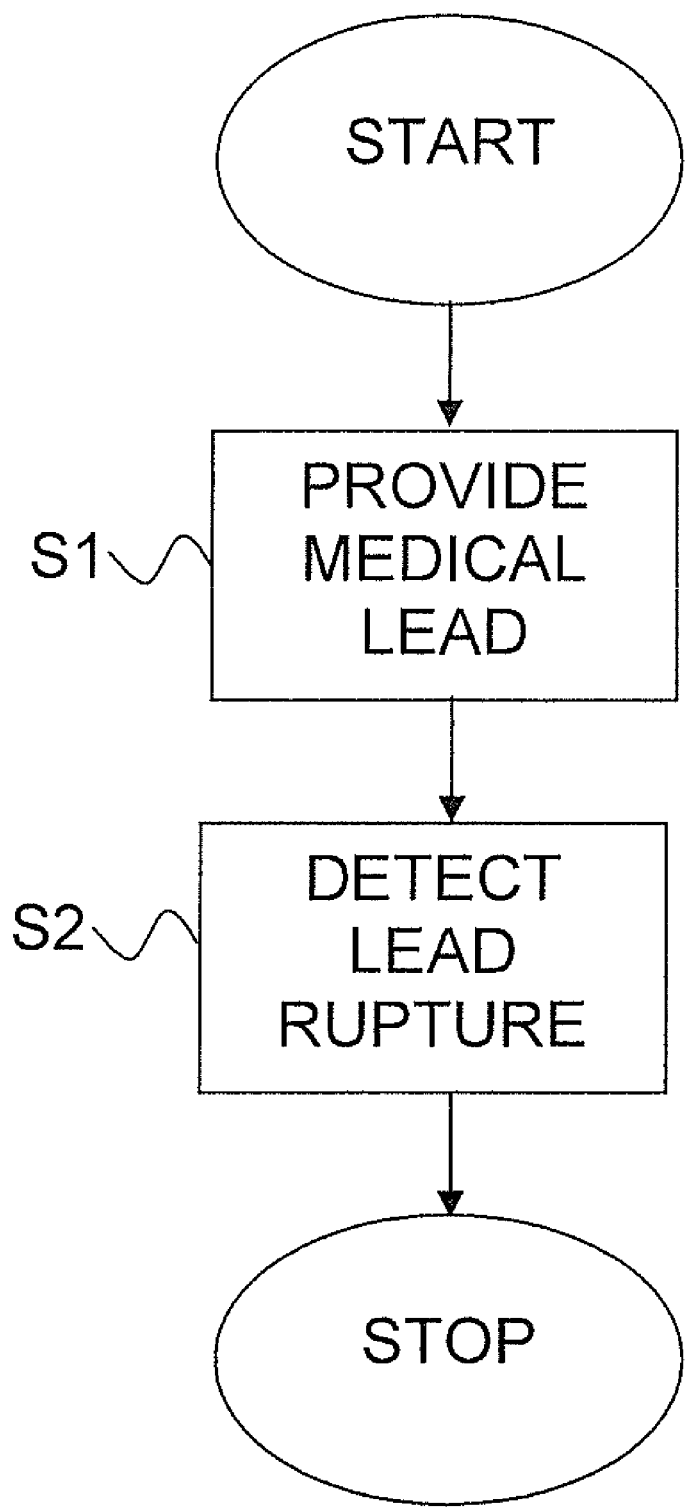
FIG. 7 is a method of detecting a rupture in an implantable medical lead according to an embodiment.

FIG. 7 is a flow diagram illustrating a method of detecting a lead insulation rupture in an implantable medical lead. The method starts in step S1 where an implantable medical lead according to the invention having at least one closed channel comprising a detection substance is provided and implanted in a human or animal body. A reduced amount of the detection substance in the closed channel is then used in step S2 as a confirmation of a lead insulation rupture.

If the detection fluid is an X-ray opaque substance, the detection in step S2 preferably involves taking at least one X-ray image or picture of at least a portion of the implantable medical lead in order to detect the absence or reduced amount of the X-ray opaque substance inside the implantable medical lead.

If the detection substance instead is a urine-coloring substance, the detection of step S2 preferably involves detecting the presence of the detection substance in the urine of the subject.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

Although modifications and changes may be suggested by those skilled in the art, it is the intention of the inventor to embody within the patent warranted hereon all changes and modifications as reasonably and properly come within the scope of his contribution to the art.

We claim:

1. An implantable medical lead comprising:
   A lead body;
   At least one lead terminal arranged in connection with a first portion of said lead body and constructed to be electrically configured for connection to a matching terminal of an implantable medical device;
   At least one electrode arranged in connection with a second, opposite portion of said lead body;
   At least one electric conductor running along said lead body and being electrically connected to said at least one lead terminal and said at least one electrode and
   At least one closed channel running along at least a portion of said lead body and comprising an extracorporeally detectable detection substance at an initial amount with a reduced amount of said detection substance in said at least one closed channel confirming a lead insulation rupture causing said detection substance to leak out of said at least one closed channel and outside of said implantable medical lead;
   Wherein said at least one closed channel comprises multiple closed chambers separated by respective walls, each of said multiple closed chambers comprising said detection substance;
   Wherein each of said multiple closed chambers comprises a differing detection substance to identify more accurately where along said lead body a rupture has occurred by identifying said particular detection substance that leaks outside of said implantable medical lead.

2. The implantable medical lead according to claim 1, wherein said at least one electric conductor comprises a coiled electric conductor having a closed inner lumen that constitutes a closed channel comprising said detection substance.

3. The implantable medical lead according to claim 1, wherein said at least one electric conductor comprises an electric conductor centrally positioned inside said body of said implantable medical lead, and wherein said at least one closed channel is peripherally positioned relative said electric conductor.

4. The implantable medical lead according to claim 1, wherein said multiple closed channels are peripherally positioned around said electric conductor.

5. The implantable medical lead according to claim 1, wherein said detection substance is a detection fluid.

6. The implantable medical lead according to claim 1, wherein said detection substance is a radio-opaque substance.

7. The implantable medical lead according to claim 1, wherein said detection substance is an X-ray opaque substance.

8. The implantable medical lead according to claim 1, wherein said detection substance is a coloring substance that is visually identifiable in urine expelled from a subject having said implantable medical lead implanted in said subject.

9. The implantable medical lead according to claim 1, wherein said detection substance is a solid substance.

10. The implantable medical lead according to claim 9, wherein said solid substance is a powder.

11. A method of detecting a lead insulation rupture in an implantable medical lead comprising:
    Forming at least one closed channel running along at least a portion of a lead body in said implantable medical lead;
    Separating the at least one closed channel into a proximal closed chamber and a distal closed chamber by a wall;
    Providing an extracorporeally detectable detection substance in said proximal closed chamber and said distal closed chamber; and
    Extracorporeally detecting a lead insulation rupture in said implantable medical lead based on a reduced amount of said detection substance in said proximal closed chamber and/or distal closed chamber;
    Wherein said proximal closed chamber and said distal closed chamber comprises a differing detection substance to identify more accurately where along said lead body a rupture has occurred by identifying said particular detection substance that leaks outside of said implantable medical lead.

12. The method according to claim 11, comprising:
    providing said implantable medical lead with a radio-opaque substance as said detection substance; and
    detecting said lead insulation rupture in said implantable medical lead by obtaining at least one X-ray image of at least a portion of said implantable medical lead in order to detect an absence or reduced amount of said detection substance in said proximal closed chamber and/or distal closed chamber.

13. The method according to claim 11, comprising:
    providing said implantable medical lead with a substance that is detectable in urine of a subject in whom said medical lead is implanted, as said detection substance; and
    detecting said lead insulation rupture in said implantable medical lead by a presence of said detection substance in expelled urine from said subject.

* * * * *